US012567504B2

(12) United States Patent
Receveur et al.

(10) Patent No.: US 12,567,504 B2
(45) Date of Patent: Mar. 3, 2026

(54) AUTOMATED MOBILITY ASSESSMENT

(71) Applicant: Hill-Rom Services, Inc., Batesville, IN (US)

(72) Inventors: Timothy Receveur, Apex, NC (US); Eugene Urrutia, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 550 days.

(21) Appl. No.: 16/951,486

(22) Filed: Nov. 18, 2020

(65) Prior Publication Data

US 2021/0158965 A1 May 27, 2021

Related U.S. Application Data

(60) Provisional application No. 62/939,107, filed on Nov. 22, 2019.

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/0077* (2013.01); *A61B 5/1124* (2013.01);
(Continued)

(58) Field of Classification Search
CPC ........ G16H 50/30; G16H 40/67; G16H 40/20; G16H 10/60; G16H 50/70; G16H 50/20;
(Continued)

(56) References Cited

U.S. PATENT DOCUMENTS 4,998,939 A * 3/1991 Potthast ................. A61G 7/052
5/424
7,682,308 B2 3/2010 Hendrich
(Continued)

FOREIGN PATENT DOCUMENTS

EP 1 216 400 B1 10/2009
EP 3553786 A1 10/2019

OTHER PUBLICATIONS

Henrich et al., "Validation of the Hendrich II Fall Risk Model: A large concurrent case/control study of hospitalized patients," Applied Nursing Research, vol. 16, Issue 1 dated Feb. 2003, pp. 9-21.
(Continued)

*Primary Examiner* — Marc Q Jimenez
*Assistant Examiner* — Rachael Sojin Stone
(74) *Attorney, Agent, or Firm* — Merchant & Gould P.C.

(57) ABSTRACT

Automatically evaluating a level of mobility of a patient using a machine-learning model and load sensors integrated into a patient support system. A machine-learning model implemented on a computing system analyzes the load sensor data to determine whether the patient has difficulty standing up. This automated analysis can replace existing mobility assessments that were previously performed by caregivers. The mobility assessment data generated by the computing system can be recorded in the patient's electronic medical record (EMR) and utilized as a factor in determining patient fall risk.

17 Claims, 9 Drawing Sheets

(51) Int. Cl.

| | |
|---|---|
| *A61B 5/11* | (2006.01) |
| *G16H 10/60* | (2018.01) |
| *G16H 40/20* | (2018.01) |
| *G16H 40/67* | (2018.01) |
| *G16H 50/20* | (2018.01) |
| *G16H 50/70* | (2018.01) |

(52) U.S. Cl.

CPC .......... *A61B 5/6892* (2013.01); *A61B 5/7267* (2013.01); *A61B 5/7275* (2013.01); *A61B 5/746* (2013.01); *G16H 10/60* (2018.01); *G16H 40/20* (2018.01); *G16H 40/67* (2018.01); *G16H 50/20* (2018.01); *G16H 50/70* (2018.01); *A61B 2562/0252* (2013.01); *A61B 2576/00* (2013.01)

(58) Field of Classification Search

CPC ... A61B 5/0077; A61B 5/1124; A61B 5/6892; A61B 5/7267; A61B 5/7275; A61B 5/746; A61B 2562/0252; A61B 2576/00

USPC .......................................................... 705/2

See application file for complete search history.

(56) References Cited

U.S. PATENT DOCUMENTS

| | | | | |
|---|---|---|---|---|
| 7,988,647 | B2 | 8/2011 | Bunn et al. | |
| 8,266,742 | B2 | 9/2012 | Andrienko | |
| 8,381,336 | B2 | 2/2013 | Kazuno et al. | |
| 8,466,801 | B2 | 6/2013 | Hayes et al. | |
| 9,471,541 | B1 * | 10/2016 | Chan | G01P 21/00 |
| 9,795,322 | B1 * | 10/2017 | Karunaratne | A61B 5/6891 |
| 11,872,169 | B2 * | 1/2024 | Newkirk | G05B 15/02 |
| 2006/0059814 | A1 * | 3/2006 | Metz | G01G 19/445 |
| | | | | 52/309.8 |
| 2010/0045474 | A1 | 2/2010 | Hayes et al. | |
| 2010/0049095 | A1 * | 2/2010 | Bunn | G16H 40/60 |
| | | | | 600/595 |
| 2012/0137436 | A1 * | 6/2012 | Andrienko | G16H 40/63 |
| | | | | 5/600 |
| 2012/0253142 | A1 * | 10/2012 | Meger | A61B 5/7221 |
| | | | | 600/301 |
| 2013/0211291 | A1 * | 8/2013 | Tran | G16Z 99/00 |
| | | | | 600/595 |
| 2016/0058326 | A1 * | 3/2016 | Winfree | A61B 5/6807 |
| | | | | 600/592 |
| 2017/0224253 | A1 * | 8/2017 | Berlin | G08B 21/22 |
| 2018/0068179 | A1 * | 3/2018 | Derenne | G08B 21/0476 |
| 2018/0125414 | A1 * | 5/2018 | Lafleche | A61G 7/05776 |
| 2018/0192923 | A1 * | 7/2018 | Fu | A61B 5/1115 |
| 2018/0230221 | A1 * | 8/2018 | Tanko | A61P 17/02 |
| 2019/0307405 | A1 * | 10/2019 | Terry | G16H 10/60 |

OTHER PUBLICATIONS

Wall et al., "The timed get-up-and-go test revisited: Measurement of the component tasks," Journal of Rehabilitation Research and Development, vol. 37, No. 1, dated Jan./Feb. 2000, pp. 109-114.

Tao et al., "Gait analysis using wearable sensors," Sensors Journal (ISSN 1424-8220), dated 2012, pp. 2255-2283.

Tinetti, "Performance-oriented assessment of mobility problems in elderly patients," Journal of the American Geriatrics Society, vol. 34, Issue 2, dated 1986, pp. 119-126.

Ugbolue et al., "The evaluation of an inexpensive, 2D, video based gait assessment system for clinical use, " Gait & Posture, vol. 38, Issue 3, dated 2013, pp. 483-489.

U.S. Appl. No. 16/913,158, filed Jun. 26, 2020, 25 pages.

Extended European Search Report for Application No. 20208641.9 mailed May 21, 2021.

European Office Action for Application No. 20208641.9 mailed Jun. 4, 2024.

Hong, "Smart Care Beds for Elderly Patients with Impaired Mobility," Wireless Communications and Mobile Computing, vol. 2018, Article ID 1780904, 12 pages, https://doi.org/10.1155/2018/1780904 (2018).

Mathias et al., "Balance in elderly patients: the "get-up and go" test," Archives of Physical Medicine and Rehabilitation, vol. 67, No. 6, pp. 387-389 (Jun. 1986) (1 page Abstract).

* cited by examiner

200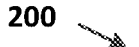
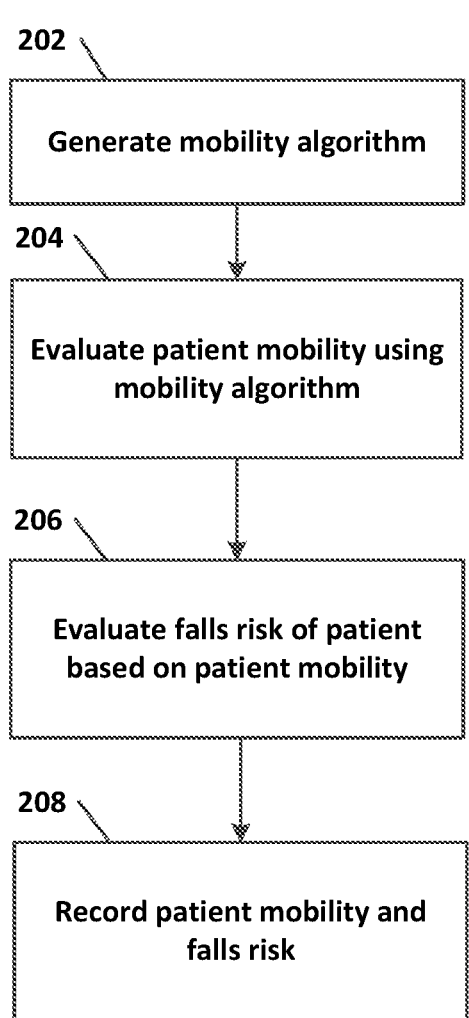
202
Generate mobility algorithm
204
Evaluate patient mobility using mobility algorithm
206
Evaluate falls risk of patient based on patient mobility
208
Record patient mobility and falls risk
FIG. 3

300

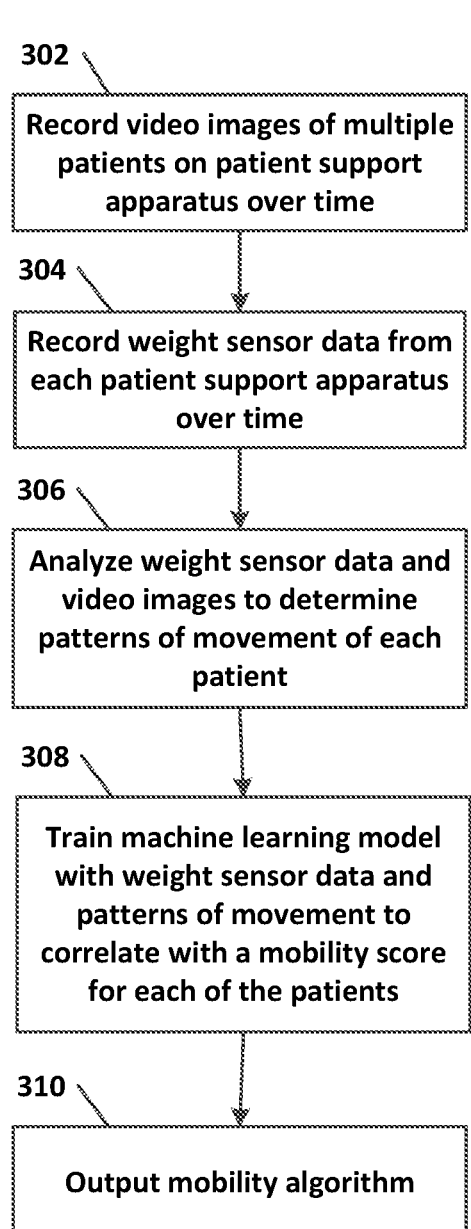

302

Record video images of multiple patients on patient support apparatus over time

304

Record weight sensor data from each patient support apparatus over time

306

Analyze weight sensor data and video images to determine patterns of movement of each patient

308

Train machine learning model with weight sensor data and patterns of movement to correlate with a mobility score for each of the patients

310

Output mobility algorithm

FIG. 4

350
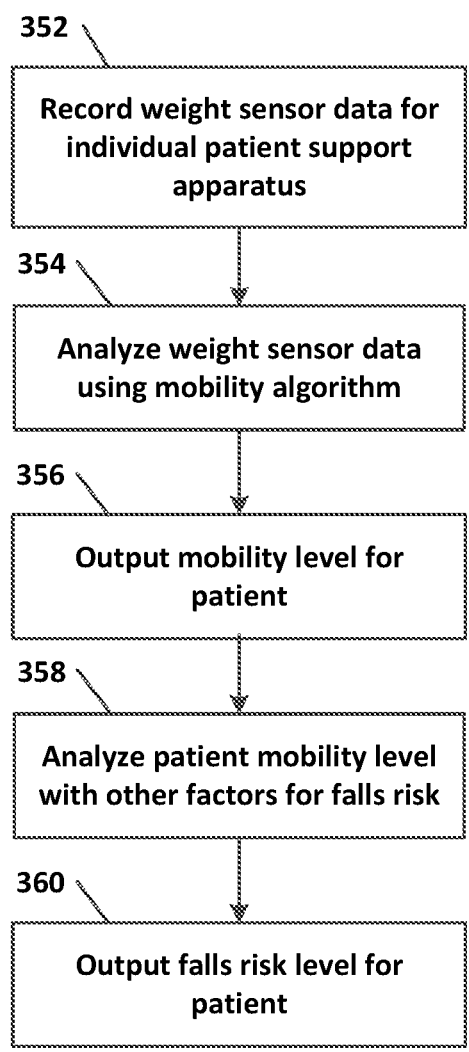
352
Record weight sensor data for
individual patient support
apparatus
354
Analyze weight sensor data
using mobility algorithm
356
Output mobility level for
patient
358
Analyze patient mobility level
with other factors for falls risk
360
Output falls risk level for
patient
FIG. 5

AUTOMATED MOBILITY ASSESSMENT

BACKGROUND

Patients in care facilities, such as hospitals, clinics, nursing homes and the like, are often in compromised medical conditions. Injuries sustained by patients due to falls in care facilities result in significant healthcare costs. In an effort to prevent such injuries, various protocols are implemented to mitigate the risks. For example, patients who are at risk of falling when moving unassisted may be identified as fall risks, and certain protocols may be implemented to reduce the opportunity for the patients to move about the room unassisted.

Multiple factors go into determining fall risk. The combination of factors may vary depending on the particular type of patient assessment. For example, the Hendrich II Fall Risk Model™ utilizes a number of different risk factors, each worth a number of risk points. If the total risk points is 5 or greater, the patient is considered "high risk" for falls. One factor that may be taken into account is a patient's level of mobility.

The "Get-Up-and-Go Test" can be used to assess mobility by classifying a patient's level of mobility into one of four predefined categories, by assessing the patient's ability to rise up from a seated position. The more difficulty the patient has in doing so, the higher the risk points. For example, a patient who is able to rise from a seated position in a single movement without loss of balance is assigned 0 risk points. A patient who is unable to rise without assistance is assigned 4 risk points. This assessment is administered by a caregiver based on observation of the patient.

SUMMARY

Embodiments of the disclosure are directed to a system and method for automatically evaluating a level of mobility of a patient. A mobility score generated by a machine-learning model can be used in conjunction with other patient information to assess patient falls risk.

In one aspect, a system for automatically evaluating a level of mobility of a patient, the system comprises: a patient support system comprising at least one load sensor; at least one processor in communication with the at least one load sensor and the camera; and memory encoding instructions. When the instructions are executed by the at least one processor, it causes the at least one processor to: record load sensor data from the patient support system for a length of time for each of a plurality of patients; determine a level of mobility of each of the plurality of patients during the length of time based on observations of patient movements; train a machine-learning algorithm with the load sensor data and corresponding level of mobility of each patient to identify patterns of load sensor data indicative of particular levels of mobility; and output a mobility model operable to determine a level of mobility of a patient based on load sensor data. An individual patient can be evaluated by: recording load sensor data from an individual patient on an individual patient support system; analyzing the load sensor data using the mobility model; and outputting a level of mobility for the individual patient.

In another aspect, a method of automatically evaluating a level of mobility of a patient comprises: recording load data received from load sensors embedded in a patient support system; analyzing the load data at a computing system using a mobility model; and outputting a level of mobility for the patient. The mobility model can be generated by: observing movements of a plurality of patients for a length of time, each patient being on a patient support system; determining mobility scores for each of the plurality of patients based on the observed movements; recording load data from each patient support system for the length of time; correlating observed movements and mobility scores with patterns of load data; and training a machine-learning algorithm with the load data and corresponding mobility scores to identify patterns of load sensor data indicative of patient movements corresponding to mobility scores.

In yet another aspect, one or more computer-readable media having computer-executable instructions embodied thereon that, when executed by one or more computing devices, cause the computing devices to: generate a mobility model by: recording over a period of time with a video camera, video images of each of a plurality of patients on patient support systems; recording over the period of time with load boards embedded in the patient support systems, load data for each of the plurality of patients; analyzing the load data and video images with a patient movement analyzer to determine patterns of movement of each patient; assigning a mobility score to each pattern of movement based on a caregiver evaluating the video images corresponding to the pattern of movement with a mobility test; training a supervised machine-learning algorithm with the load sensor data and corresponding mobility scores to output a mobility model; and evaluate an individual's level of mobility by: recording load sensor data for an individual patient from one or more load boards embedded in a patient support system of the individual patient; and analyzing the load sensor data with the mobility model; evaluate the individual's fall risk by: analyzing the individual patient's mobility level with other factors of a fall risk assessment, wherein the other factors are determined by one or more of receiving input from a caregiver, accessing information from the patient's EMR, and receiving data from a patient monitoring device; record the individual patient's mobility score and fall risk level in the patient's EMR; and if the patient's mobility score or falls risk level exceed a predetermined threshold, issue an alert to a hospital information system.

The details of one or more techniques are set forth in the accompanying drawings and the description below. Other features, objects, and advantages of these techniques will be apparent from the description, drawings, and claims.

DESCRIPTION OF THE DRAWINGS

FIG. 3 is a flow chart illustrating an example method of automatically assessing patient fall risk using a mobility model.

FIG. 4 is a flow chart illustrating an example method of generating a mobility model.

FIG. 5 is a flow chart illustrating an example method of automatically evaluating patient mobility and fall risk.

DETAILED DESCRIPTION

The present disclosure is directed to systems and methods for automatically evaluating a level of mobility of a patient. Load sensors integrated into a patient support system record patient movements. An algorithm implemented on a computing device is used to analyze the recorded patient movements to determine whether the patient has difficulty standing up. This analysis can replace existing mobility assessments that were previously performed manually by caregivers.

Mobility assessment data generated by the computing device can be recorded in the patient's electronic medical record (EMR) and utilized as a factor in determining patient fall risk. The machine-learning model can be generated using a machine-learning algorithm trained on load sensor data combined with mobility assessments done based on video of patients.

Figure 1:
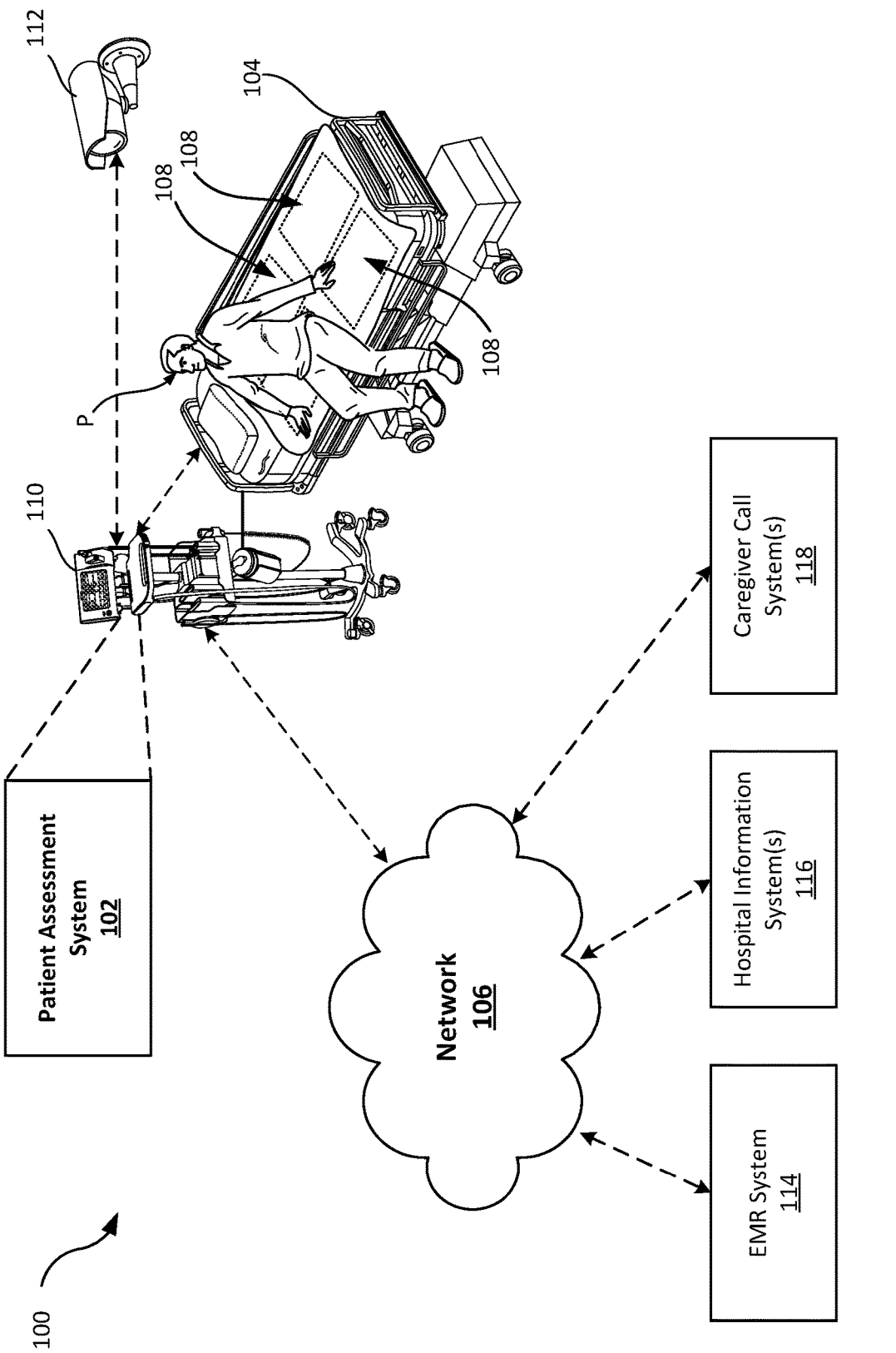
FIG. 1 is a schematic diagram illustrating an example system for automatically evaluating a level of mobility of a patient.

FIG. 1 is a schematic diagram illustrating an example system 100 for evaluating patient mobility. The system 100 includes a patient assessment device 102 and a patient support system 104 in communication with a network 106. In some embodiments, the patient support system 104 includes a plurality of load sensors 108. The system 100 can also include a camera 112. In some embodiments, the patient support system 104 (including the load sensors 108) is in communication with a patient monitoring computing device 110. The camera 112 is also in communication with the patient monitoring computing device 110. The patient monitoring computing device 110 is in communication with the patient assessment device 102 through the network 106. In some embodiments, the camera 112 and patient support system 104 communicate directly with the patient assessment device 102 without utilizing a patient monitoring computing device 110 to mediate communication through the network 106. In such embodiments, the patient support system 104 includes a processor and memory. In some embodiments, the system 100 includes one or more of an electronic medical record (EMR) system 114, a hospital information system 116 and a caregiver call system 118.

The patient assessment device 102 operates to receive, process, and send information related to determining a patient's level of mobility and risk of falling. One or more assessments for mobility and risk of falling can be automatically implemented by the patient assessment device 102 using data received from one or more of the patient support system 104, patient monitoring computing device 110, camera 112, and EMR system 114. Examples of such assessments include the Timed Get Up and Go test, the Hendrich II Fall Risk Model, and the Tinettia Balance and Gait Test.

The patient support system 104 operates to provide a surface for a patient to rest upon while under medical care. The patient support system 104 can be one or more of a bed, a chair, a lift, and/or a surgical table.

The patient support system 104 includes a plurality of load sensors 108. In some embodiments, the load sensors 108 are weight-measuring devices that include load boards, load cells, and strain gauges. In some embodiments, there are at least two load sensors 108. In some embodiments, there are at least 3 load sensors 108. In some embodiments, there are at least 4 load sensors embedded in the patient support system 104.

The network 106 operates to mediate communication of data between network-enabled computing systems. In various embodiments, the network 106 includes various types of communication links. For example, the network 108 can include wired and/or wireless links, including cellular, Bluetooth, ultra-wideband (UWB), 802.11, ZigBee, and other types of wireless links. The network 106 can include one or more routers, switches, mobile access points, bridges, hubs, intrusion detection devices, storage devices, standalone server devices, blade server devices, sensors, desktop computers, firewall devices, laptop computers, handheld computers, mobile telephones, vehicular computing devices, and other types of computing devices.

Figure 7:
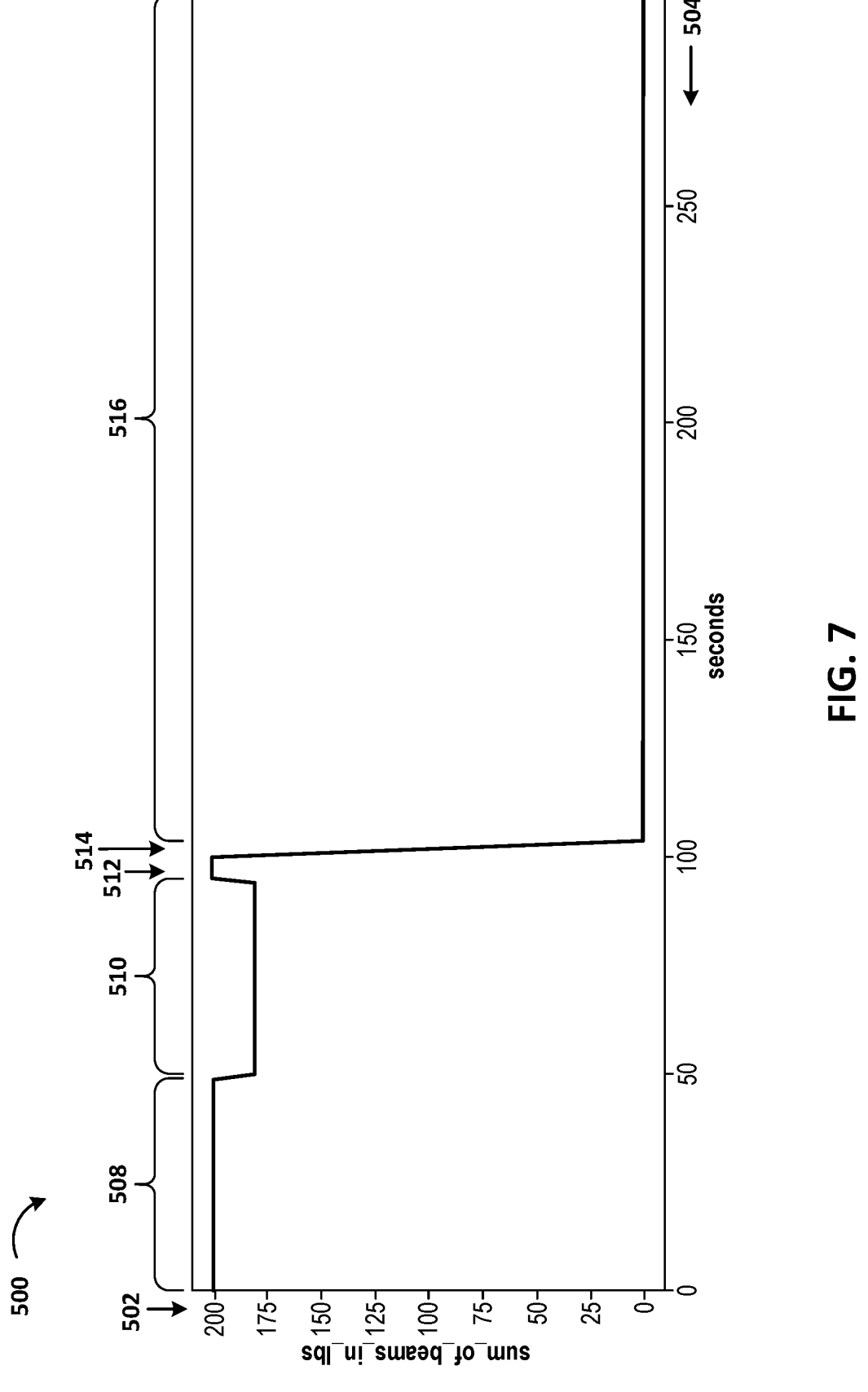
FIG. 7 illustrates an example display output of load beam data obtained from patient support system of the system of FIG. 1.
Figure 8:
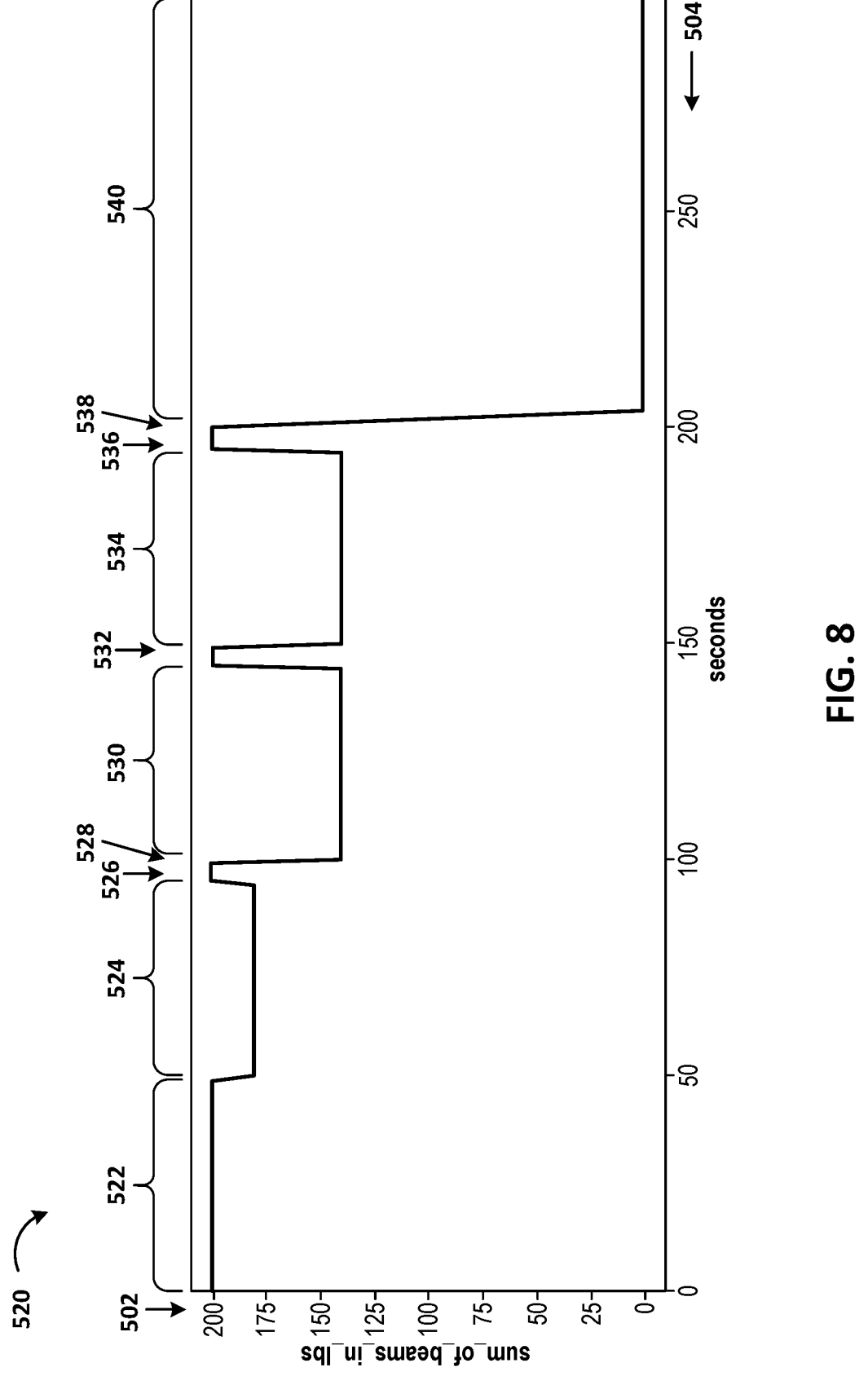
FIG. 8 illustrates another example display output of load beam data obtained from the patient support system of the system of FIG. 1.
Figure 9:
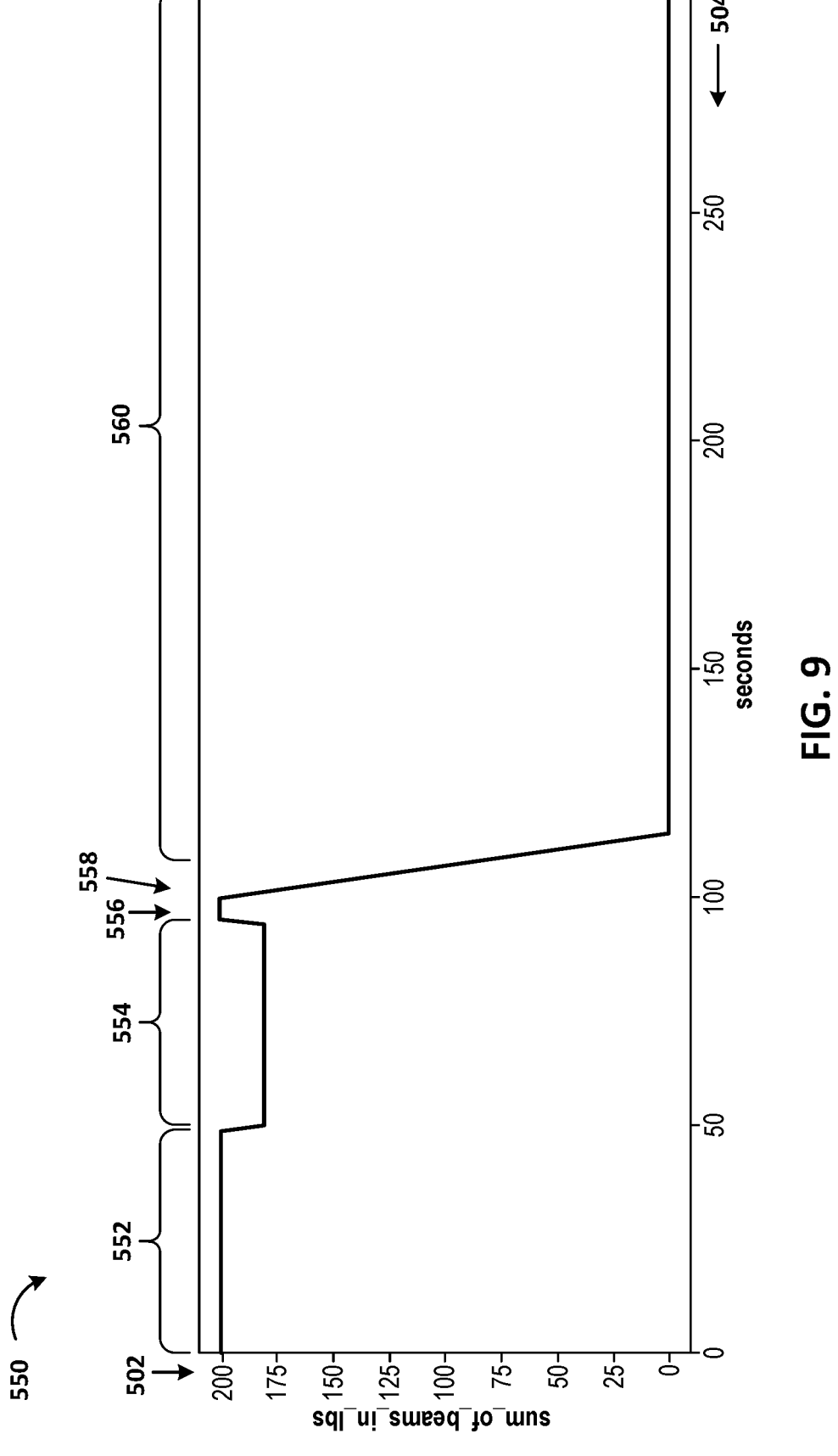
FIG. 9 illustrates another an example display output of load beam data obtained from the patient support system of the system of FIG. 1.

The load sensors 108 operate to determine a total weight that is on the patient support system 104. If there is more than one load sensor 108, the load sensors work together to produce an aggregate weight total for the whole patient support system 104. Information about a patient's movements to stand up and off the patient support system 104 can be inferred from recording the total weight on the patient support system 104 over time. Attempts to stand could be inferred from reductions in weight, but not a removal of all weight from the patient support system 104. A successful attempt to get off the patient support system 104 can be inferred from all weight being removed. Example outputs of the load sensors 108 are shown in FIGS. 7-9.

The patient monitoring computing device 110 operates to receive and record data for a particular patient from one or more patient monitoring devices. The patient monitoring devices are in communication with the patient monitoring computing device 110 through a wired or wireless connection. Examples of patient monitoring devices include heart rate monitors, pulse oximeters, etc. In some embodiments, the patient monitoring devices can include the camera 112 and load sensors 108 of the patient support system 104.

In some embodiments, the patient monitoring computing device 110 includes a processor and memory device. The memory device can include instructions for the processor to analyze data received from patient monitoring devices. In some embodiments, the memory device can also store patient data locally. The patient monitoring computing device 110 can include a display and a user interface face that allows a caregiver to easily access patient data. In some embodiments, patient monitoring computing device 110 communicates patient data to one or more of the patient assessment device 102, EMR system 114, hospital information system 116 and caregiver call system 118 through the network 106. In some embodiments, data is automatically communicated from the patient monitoring computing device 110 to the patient assessment device 102.

The camera 112 operates to capture images of a patient on a patient support system 104 to monitor patient movements. In some embodiments, the camera is triggered by movement as detected by infrared sensors or other motion-detectors. This ensure that video is recorded of patients getting out of bed, but will not record an empty room or a sleeping patient. In some embodiments, images of the patient are blurred before recording the video to storage in order to protect the patient's privacy. In some embodiments, the system 100 does not include a camera 112 and instead relies on caregiver observations.

The electronic medical record (EMR) system 114 operates to record information relevant to the medical history of each patient. Examples of information that might be stored in a patient's EMR includes lab results, surgical history, family medical history, current medications, and previous medical diagnoses. A patient's fall risk score (as determined by e.g.

Morse Fall Scale, Johns Hopkins Fall Risk Assessment Tool, etc.) or sub-score (as determined by Get Up and Go test) are other pieces of information that could be added to an EMR. Examples of electronic medical records systems 114 include those developed and managed by Epic Systems Corporation, Cerner Corporation, Allscripts, and Medical Information Technology, Inc. (Meditech).

The hospital information systems 116 operate to record, store, and communicate information about patients, caregivers, and hospital facilities. Examples of hospital information system 116 include admit/discharge/transfer (ADT) systems. ADT systems operate to record, store, and communicate information about patient demographics.

The caregiver call systems 118 operate to generate alerts that are triggered by one or more rules. The alerts are sent to caregivers that need to perform critical tasks. The alerts can be generated based on data from the vital signs monitoring devices or updates to patient information that are received at the EMR system 114. As an illustrative example, patient fall risk scores, when above a predetermined threshold, trigger an alert from caregiver call system 118 that is sent to a computing device associated with a caregiver so that the caregiver is notified of the need to perform critical tasks based on the patient's fall risk.

In some embodiments, the system further includes a plurality of location monitoring devices configured to track locations of caregivers and patients. The location monitoring devices can help to ascertain whether load detected on a patient support system 104 is caused by a patient or a caregiver as well as determine whether a caregiver is present to aid a patient when the patient is getting off a patient support system 104.

Figure 2:
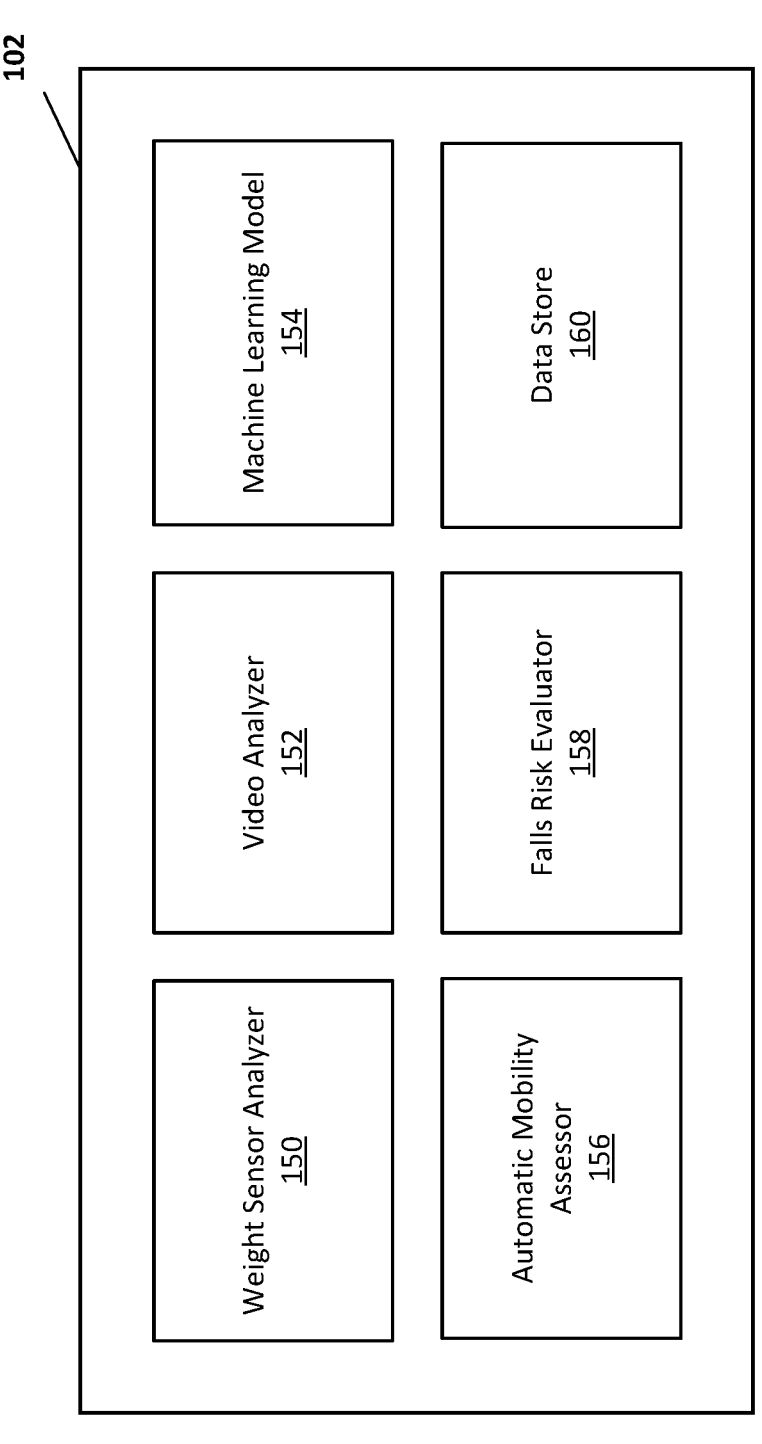
FIG. 2 is a schematic diagram illustrating details of a patient assessment device of the system of FIG. 1.

FIG. 2 is a more detailed schematic diagram of the patient assessment device 102 of FIG. 1. The patient assessment device 102 includes a patient movement analyzer 152, a machine-learning algorithm 154, an automatic mobility assessor 156, a falls risk evaluator 158, and a data store 160. The patient assessment device 102 can operate locally at a patient support system or a patient monitoring computing device 110 in communication with a patient support system. In some embodiments, the patient assessment device 102 can operate on a remote server in communication with one or more patient support systems.

The patient movement analyzer 152 operates to receive and analyze video and load sensor data for a plurality of patients on a plurality of patient support systems. The video and load sensor data is correlated by time to match activity recorded on the load sensors with visually confirmed patient movements. In some embodiments, a caregiver reviews video recordings to assess the patient's mobility level according to a mobility assessment. In other embodiments, the caregiver inputs a mobility level or score into a computing device after assessing the patient. The input is recorded in the patient's EMR and is accessible by the patient movement analyzer 152. The patient movement analyzer 152 operates to identify patterns in the load sensor data that indicate activity of interest is occurring, such as a patient getting out of bed.

The machine-learning algorithm 154 is generated using the load sensor data and the visually confirmed mobility scores of patients. In some embodiments, the machine-learning algorithm is a supervised machine-learning algorithm. Examples of supervised machine-learning algorithms that could be utilized include support vector machines, gradient boost machine, neural networks, and logistic regression. Patterns in the load sensor data and the corresponding mobility score are paired and used as labeled inputs to train the algorithm. In some embodiments, another set of load sensor data and corresponding mobility scores are used to validate the machine-learning model. The machine-learning algorithm 154 produces a mobility model usable by the automatic mobility assessor 156. In some embodiments, the machine-learning algorithm 154 is updated using feedback from analysis performed by the automatic mobility assessor 156.

For instance, in one example, the mobility model can be based on the following equation:

$$\text{Current Load Board data+Historic Load Board data=Mobility Level}$$

In certain examples, the load board data over a particular period is assessed as a particular event. For instance, the system can detect when the current load board data indicates that the patient is moving toward an exit of the patient support system (e.g. getting ready to stand up from a chair or bed). At this instance, the system can track current load board data as compared with historic load board data over the event duration to assess mobility. In some examples, the event duration can be 5 seconds, 10 seconds, 30 seconds, or another defined and/or variable duration.

In other examples, further information can be added to refine the mobility model. An example of such a mobility model can be based on the equation:

$$\text{Current Load Board data+Historic Load Board data+Other Factors=Mobility Level}$$

In this example, the other factors can include demographic information (e.g., gender, age, etc.) and/or specific medical information about the patient (e.g., physical limitations, drug regime, etc.). Other configurations are possible.

The automatic mobility assessor 156 utilizes the mobility model generated by the machine-learning algorithm 154 to analyze load sensor data from individual patient support systems to assess the individual patient's level of mobility. The automatic mobility assessor 156 may perform all or part of a patient mobility assessment. Examples of mobility assessments that can be at least partially automated include the Timed Get-Up-and-Go Test. In some embodiments, the Get-Up-and-Go Test can be completely automated using the automatic mobility assessor 156.

The falls risk evaluator 158 operates to combine the mobility assessment performed by the automatic mobility assessor 156 with other patient data and/or caregiver inputs to complete a falls risk assessment for a patient. In some embodiments, at least some portions of the falls risk assessment (other than mobility) are automated based on patient data that is automatically gathered from a patient monitoring device or is automatically accessed from electronic records.

In the example of the Hendrich II Fall Risk Model™, the automatic mobility assessor 156 can perform the Get-Up-and-Go Test based on the load sensor data. However, other risk factors of the Hendrich II Fall Risk Model™, such as "confusion/disorientation/impulsivity" or "symptomatic depression," require caregiver input. However, given that a total score of 5 results in an assessment of "High Risk," a score of 3 or 4 on the Get-Up-and-Go Test would factor for the majority of a determination that a patient is at a high falls risk. In that situation, it is possible that in combination with one or more risk factors that can be easily assessed based on the patient's EMR (e.g. administered antiepileptics, administered benzodiazepines), the entire fall risk evaluation could be automated for a patient.

The data store 160 operates to store various collections of data utilized by the patient assessment device 102. For example, the data store 160 could temporarily store load sensor data and video recordings that will be used to train the machine-learning algorithm 154. The data store 160 could also operate to store the mobility model or a mobility score generated for a particular patient.

FIG. 3 is a flow chart illustrating an example method 200 of automatically assessing patient fall risk using a mobility model. This method 200 can be performed by the systems described in FIGS. 1-2.

At operation 202, a mobility model is generated. Multiple patients are observed while data is gathered from load sensors in their hospital beds. The load sensor data for each patient is followed over a length of time to identify patterns indicating that a patient is getting out of bed. In some embodiments, the length of time is at least 5 seconds, at least 10 seconds, at least 30 seconds, or at least 1 minute. These patterns are used to train a machine-learning algorithm to produce the mobility model. This process is described in detail in FIG. 4.

At operation 204, patient mobility is automatically evaluated using the mobility model generated in operation 202. Evaluations are performed on individual patients to determine a mobility sub-score that can be used to evaluate patient fall risk when combined with other information. Load sensor data for the patient's bed is gathered over time. The load sensor data is analyzed using the mobility model to produce a mobility score for the patient. This process is described in greater detail in FIG. 5

At operation 206, falls risk of the patient is evaluated based on the mobility score determined in operation 204. Additional factors are considered to determine a patient's fall risk depending on the particular falls risk assessment utilized. In some embodiments, the fall risk assessment is completely automated and utilizes information obtained from the patient's EMR to supplement the mobility score. In other embodiments, caregiver input is required to complete the assessment. This process is described in greater detail in FIG. 5

At operation 208, the patient's mobility score and falls risk assessment are recorded. In some embodiments, they are recorded in an electronic record such as the patient's electronic medical record (EMR). In some embodiments, the mobility score and risk assessment are recorded locally at the bed or a computing system in communication with the bed. This process is described in greater detail in FIG. 5.

FIG. 4 illustrates a flow chart of an example method 300 of generating a mobility model. In some embodiments, this method 300 is performed by the patient assessment device 102 of FIG. 1. In particular, the patient movement analyzer 152 and machine-learning algorithm 154 can be implemented to perform this method 300.

At operation 302, video images of multiple patients, each on their own respective patient support system, are recorded over time. In some embodiments, a video camera positioned near the patient support system records video of the patient. The camera could be camera 112 of FIG. 1. In some embodiments, infrared sensors are used to detect motion and activate the video camera. The video captures movements of the patient that can be analyzed to determine if the patient is getting up from the patient support system and whether the patient is having difficulty doing so. In some embodiments, the video recordings are stored, permanently or temporarily, in a data store accessible by a computing device that also has access to load sensor data from the patient's bed. In some embodiments, patients are observed directly by caregivers instead of reviewing video images of the patients.

At operation 304, load sensor data from each of the patient support systems is recorded. Each of the multiple patients' movements are recorded based on changes that occur in the load detected on the bed or chair over time. In some embodiments, load sensor data is recorded from a plurality of load boards 108 embedded in a patient support system 104. In some embodiments, the load sensor data is stored in a data store accessible by a computing device that also has access to the video recordings. For example, the video recordings and load sensor data could be stored in the data store 160 of FIG. 2. In other embodiments, the video recordings and load sensor data can be recorded in separate places.

At operation 306, the load sensor data and video images are analyzed to determine patterns of movement of each patient. In some embodiments, this step is performed by the patient movement analyzer 152 of FIG. 2. Patterns in the load sensor data can be analyzed to determine whether a patient is in bed, out of bed, or getting out of bed. If the patient is in a chair, load sensors in the chair can similarly be analyzed to determine whether the patient is sitting in the chair, is not on the chair, or is getting up off the chair. In the example system of FIG. 1, the sum of the load sensors 108 can be analyzed to determine if the patient is getting out of the patient support system 104. Examples of load board data are shown in FIGS. 7-9.

Video data is analyzed and correlated to the load sensor data to match up changes in weight on the patient support system with particular movements of the patient. For example, video might confirm that a steady reading of 200 pounds on the load sensors of the patient support system are indicative of the patient lying on the patient support system. In another example, dips down in the load sensed by the load sensors on the patient support system can be correlated with video of the patient making one or more attempts to get out of bed.

For the purposes of generating a mobility model, the video is analyzed by a caregiver to determine whether the patient is matching a particular category of the mobility test. A mobility score is given to each patient based on the observed patterns of movement. In some embodiments, patient movements are observed directly by a caregiver and are recorded in the patient's EMR.

At operation 308, a machine-learning algorithm is trained. In some embodiments, data sets including load sensor data and the corresponding mobility score (as determined from video or direct observation) are used to train a supervised machine-learning algorithm. The resulting model can be used to determine a mobility score based solely on load sensor data from a patient support system. The mobility model is operable to identify patterns of load sensor data that correlate to particular levels of mobility of a patient. In some embodiments, the machine-learning algorithm is the machine-learning algorithm 154 of FIG. 2.

At operation 310, a mobility model is output. In some embodiments, the machine-learning algorithm 154 outputs the mobility model to the automatic mobility assessor 156. In some embodiments, the mobility model is stored in a data store such as the data store 160 of FIG. 2.

FIG. 5 illustrates a flow chart of an example method 350 of evaluating a patient's risk of falling while under medical care. In some embodiments, the method 350 is performed by the patient assessment device 102 of FIG. 2. In particular, the automatic mobility assessor 156 and falls risk evaluator 158 can be implemented to perform this method.

At operation 352, load sensor data from an individual patient support system is recorded. In some embodiments, the weight data is received from load beams integrated into a patient's hospital bed.

At operation 354, the load sensor data is analyzed using a mobility model. In some embodiments, this is the machine-learning model generated by the machine-learning algorithm 154 as described in FIG. 4. In some embodiments, the automatic mobility assessor 156 of FIG. 2 can be implemented to perform this analysis. As load sensor data is received over time, it is analyzed using the mobility model to detect patterns in the fluctuations of load that are detected on a patient support system. Particular patterns indicate that a patient is lying in bed, having difficulty getting out of bed, easily getting out of bed, or is currently out of the bed. In some embodiments, data is received from location monitoring devices configured to track locations of caregivers in order to determine whether a caregiver is present at the patient support device 104 at any time.

At operation 356, a mobility level or score is output for the patient. The output depends on the particular mobility assessment that is being utilized. For example, with the Get-Up-and-Go Test, a numerical score is output. If the patient is able to rise from bed (or a chair) in a single movement without losing balance (as indicated with load board data), the output is 0 risk points. If the patient takes multiple attempts to rise from the bed, but is ultimately successful, 3 risk points are output. If the patient is unable to rise without assistance, 4 risk points are output.

At operation 358, the patient's mobility level is analyzed along with other factors to evaluate the patient's falls risk. The other factors are determined based on a particular falls risk assessment. In some embodiments, the patient's mobility level is ascertained automatically from load sensor data obtained from the patient's bed, but other factors are determined by a caregiver. For example, a caregiver could access the patient's mobility score using a computing device, perform additional assessments, and then input a falls risk level or score into the computing device to be recorded with the patient's electronic records. In other embodiments, the patient's mobility level is ascertained automatically and additional factors are also determined automatically by a computing system. For example, the patient assessment device 102 could combine EMR data for a patient with the automatically determined mobility score to make an overall falls risk assessment for a patient. In some embodiments, all of the additional falls risk factors could be determined by automatically accessing the patient's EMR, assuming that the patient's information has been updated by a caregiver. In some embodiments, some factors can be determined based on data received from patient monitoring devices.

At operation 360, the falls risk level or score for the patient is output. In some embodiments, the falls risk level is recorded in the patient's EMR, for example through the EMR system 114. The output could also be to a display on a computing device, such as the patient monitoring computing device 110 of FIG. 1. Alternatively, the falls risk level could be output to a caregiver call system 118 or other hospital information system 116. In some embodiments, the falls risk level or score is utilized to automatically generate alerts to caregivers about the patient's propensity to fall or to automatically implement safety measures for high risk patients such as arming guard rails on the patient's bed.

Figure 6:
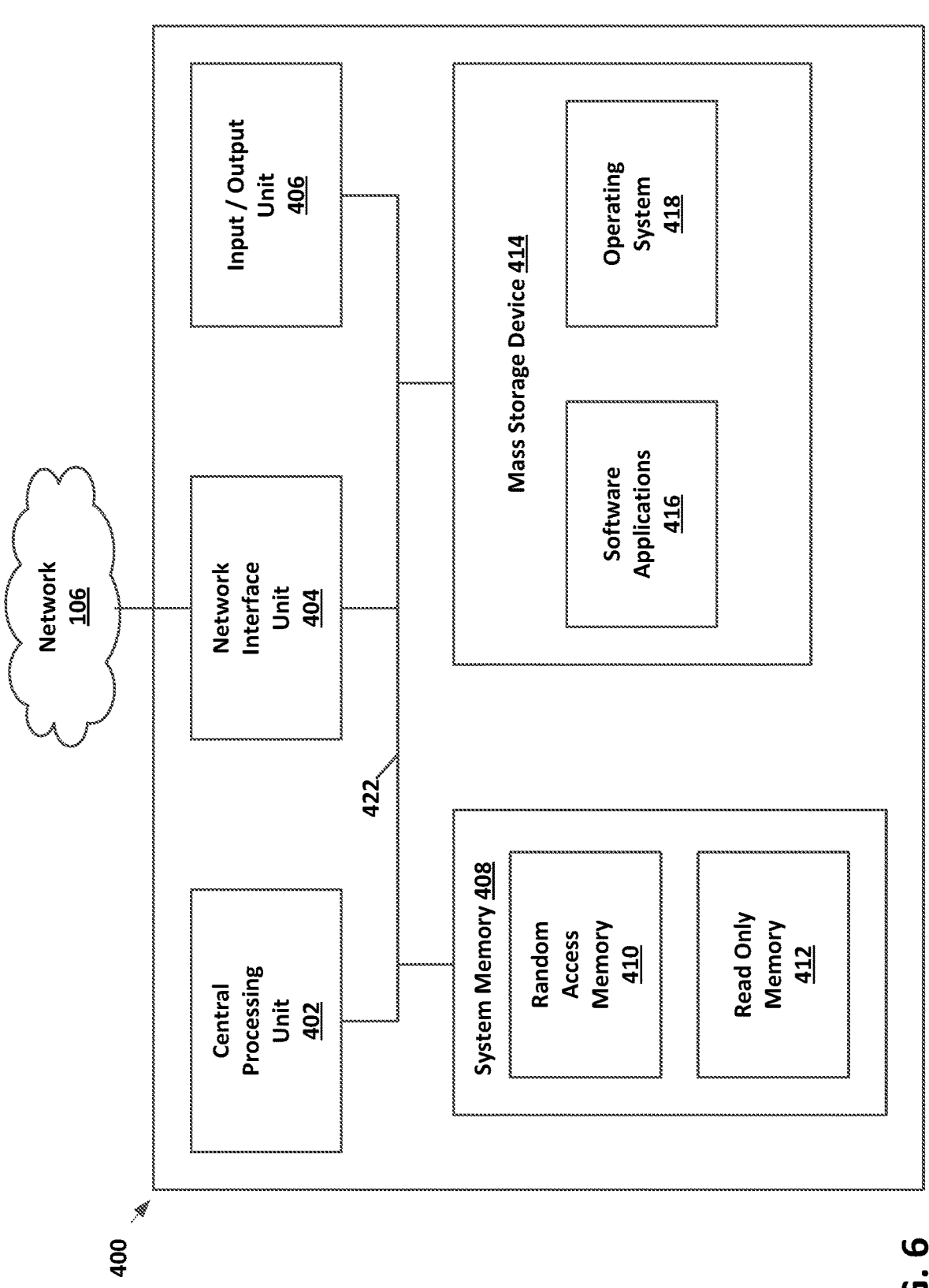
FIG. 6 is a block diagram illustrating example components of the patient assessment device of FIG. 2.

FIG. 6 is a block diagram illustrating an example of the physical components of a computing device 400. The computing device 400 could be implemented in the patient assessment device. Components of the computing device

400 can also be incorporated into other devices described herein, such as the patient monitoring computing device 110 or a computing device integrated into the patient support system 104.

In the example shown in FIG. 6, the computing device 400 includes at least one central processing unit ("CPU") 402, a system memory 408, and a system bus 422 that couples the system memory 408 to the CPU 402. The system memory 408 includes a random access memory ("RAM") 410 and a read-only memory ("ROM") 412. A basic input/output system that contains the basic routines that help to transfer information between elements within the computing device 400, such as during startup, is stored in the ROM 412. The computing system 400 further includes a mass storage device 414. The mass storage device 414 is able to store software instructions and data such as load data received from load sensors 108 embedded in the patient support device 104.

The mass storage device 414 is connected to the CPU 402 through a mass storage controller (not shown) connected to the system bus 422. The mass storage device 414 and its associated computer-readable storage media provide non-volatile, non-transitory data storage for the computing device 400. Although the description of computer-readable storage media contained herein refers to a mass storage device, such as a hard disk or solid state disk, it should be appreciated by those skilled in the art that computer-readable data storage media can include any available tangible, physical device or article of manufacture from which the CPU 402 can read data and/or instructions. In certain embodiments, the computer-readable storage media comprises entirely non-transitory media.

Computer-readable storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the computing device 400.

According to various embodiments, the computing device 400 can operate in a networked environment using logical connections to remote network devices through a network 106, such as a wireless network, the Internet, or another type of network. The computing device 400 may connect to the network 106 through a network interface unit 404 connected to the system bus 422. It should be appreciated that the network interface unit 404 may also be utilized to connect to other types of networks and remote computing systems. The computing device 400 also includes an input/output controller 406 for receiving and processing input from a number of other devices, including a touch user interface display screen, or another type of input device. Similarly, the input/output controller 406 may provide output to a touch user interface display screen or other type of output device.

As mentioned briefly above, the mass storage device 414 and the RAM 410 of the computing device 400 can store software instructions and data. The software instructions include an operating system 418 suitable for controlling the operation of the computing device 400. The mass storage device 414 and/or the RAM 410 also store software instructions, that when executed by the CPU 402, cause the computing device 400 to provide the functionality discussed in this document. For example, the mass storage device 414 and/or the RAM 410 can store software instructions that, when executed by the CPU 402, cause the computing system 400 to automatically assess a patient's level of mobility based on load sensor data.

FIGS. 7 to 9 illustrate example graphical outputs 500 of load beam data from a patient support system, such as the patient support system 104. In these examples, there are four load beams embedded in the patient bed and the cumulative weight recorded by those load beams is recorded. The y-axis 502 of the graphs represents cumulative weight in pounds. The x-axis 504 represents time of day.

The example graph 500 of FIG. 7 illustrates load beam data corresponding to a patient that is successfully getting out of bed. At 0 to 50 seconds (508), the full weight of the patient is on the bed, as shown from the sum of beams at 200 pounds (lbs). At 50 seconds (510), the patient's feet have swung over the side of the bed and are on the ground, taking some of the weight off the bed (total is about 175 lbs). At about 95 seconds (512), the patient leans back in preparation for getting up, putting more weight back on the bed. From about 100 to 105 seconds (514), the patient is leaning forward, reaching for the nurse, and rising off the bed. From about 105 seconds on (516), there is no weight on the bed.

This example graph 500 corresponds to a patient that is able to get up to a standing position from a seated position on a bed in a single attempt that takes about 5 seconds of effort. Using the Hendrich II Get Up and Go Test, this patient would be given a risk score of 0. This could be determined automatically by the automatic mobility assessor 156 of FIG. 2. Therefore, unless other risk factors indicate that the patient is a falls risk, the patient will not be deemed to have a high risk of falling. The falls risk evaluator 158 could determine the patient's overall falls risk based on a combination of the results of the Get Up and Go Test and one or more of caregiver input and accessing the patient's EMR. In this example, if the patient's EMR did not indicate that enough other falls risk factors are present (e.g. altered elimination, male gender, administered benzodiazepines), the patient's overall falls risk will remain normal.

The example graph 520 of FIG. 8 illustrates load beam data corresponding to a patient that requires multiple attempts to get out of bed. Similar to FIG. 7, the patient starts out lying on the bed (522) and then the patient's feet are on the floor at 50 seconds (524). A first attempt to get up off the bed occurs at 100 seconds (526), as shown by the brief increase in load as the patient leans back in preparation to get up, and then some of the patient's weight is lifted off the bed (528). From about 105 seconds to 145 seconds (530), the patient leans back on the bed, but does not rest all of his or her weight on the bed. Another attempt occurs at 150 seconds (532), followed by another period of rest (534). A third attempt occurs at about 200 seconds (536). Finally, the patient's attempt to stand is successful as shown by all of the patient's weight being removed from the bed at about 205 seconds (538). The remainder of the graph indicates that the patient is not on the bed (540). Using the Hendrich II Get Up and Go Test, this patient would be given a risk score of 3. If no other risk factors are identified by the falls risk evaluator 158, this patient would not be considered high risk for falls. However, if the patient's EMR indicated that the patient has been receiving antiepileptics, the patient's fall risk would be automatically designated as high by the falls risk evaluator 158.

The example graph 550 of FIG. 9 illustrates load beam data corresponding to a patient that is able to stand from a seated position in one attempt, but it takes longer to do so. As in the graph 500 of FIG. 7, the patient begins lying down (552). Again, from 50 seconds to about 95 seconds (554), the patient's feet are on the floor, taking a little weight off the bed. A little weight is transferred back to the bed as the patient is preparing to stand at 95 seconds (556). Then at 100 seconds (558), the patient is slowly leaning forward to rise up and off the bed. It takes about 15 seconds for the patient to come to a standing position. From about 115 seconds on (560), the patient is off the bed. According to the Hendrich II Get Up and Go Test, the patient would receive a risk score of 0. However, the amount of time it takes to get up can also be a useful factor in the Time Up & Go test. This test involves a patient standing from a seated position, walking 3 meters away from the bed and back, and sitting back down. The consensus is that if a patient takes longer than 12 seconds to complete the test, he or she is considered high risk for falling.

The systems and methods described herein provide technical and practical advantages over existing solutions. The manual workload of caregivers is reduced by automating at least a portion of the assessment of a patient for mobility and falls risk. This not only saves the caregiver time and effort, but also requires fewer inputs to be processed at a computing device. Previously, in order to input an assessment of mobility and/or falls risk, a caregiver would have to manually input risk scores into a patient's EMR.

The methods of assessing mobility described herein also provide the advantage of automation without requiring additional devices to be installed or worn by the patient. Additionally, no extra steps are required to set up the system. The mobility assessment is performed using information that is already being passively gathered by a patient's bed. Load board readings that were previously used for one purpose can now be utilized for two.

Finally, because the load sensors are continually gathering data at the patient's bed and analyzing that data, the methods described herein provide yet another advantage in that changes in a patient's mobility level can be detected more quickly than by having a caregiver perform periodic assessments of a patient. Thus, changes to a patient's mobility level can be responded to appropriately immediately.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A system for automatically evaluating a level of mobility of a patient, the system comprising:
   a patient support system comprising at least one load sensor, wherein the patient support system is a bed and the at least one load sensor comprises at least two load beams embedded in the bed and positioned to measure patient movements while lying on the bed;
   at least one processor in communication with the at least one load sensor; and
   a memory encoding instructions which, when executed by the at least one processor, cause the at least one processor to:
      record load sensor data from the patient support system for a length of time for each of a plurality of patients;
      determine a level of mobility of each of the plurality of patients during the length of time based on observations of the patient movements;

train a machine-learning algorithm with the load sensor data and corresponding level of mobility of each patient to identify patterns of the load sensor data indicative of particular levels of mobility;

output a mobility model operable to determine a level of a mobility of a patient based on the load sensor data;

evaluate a falls risk level of the patient based on the level of the mobility of the patient, the level of the mobility of the patient including a length of time to exit the bed, wherein the length of time is determined from when the patient is in a position on the patient support structure to when the patient is in a standing position, and wherein the length of time is compared to a range of values;

record the falls risk level of the patient; and automatically implement a safety measure on the bed based on the falls risk level by arming guard rails on the bed when the falls risk level exceeds a threshold.

2. The system of claim 1, further comprising a camera configured to capture images of the patient on the patient support system during the length of time, wherein observations of the patient movements are performed by reviewing the images captured by the camera.

3. The system of claim 1, wherein the length of time is at least 10 seconds.

4. The system of claim 1, wherein the machine-learning algorithm is a supervised machine-learning algorithm.

5. The system of claim 1, wherein if the falls risk level exceeds the threshold, an alert is issued to a hospital information system.

6. The system of claim 1, further comprising an infrared sensor configured to detect movement of the patient and activate a camera.

7. The system of claim 1, further comprising one or more location monitoring devices configured to track locations of caregivers.

8. A method of automatically evaluating a level of mobility of a patient, the method comprising:

recording load data received from load sensors embedded in a patient support system, wherein the patient support system is a bed and the load sensors comprise at least two load beams embedded in the bed and positioned to measure patient movements while lying on the bed;

analyzing the load data at a computing system using a mobility model;

outputting a level of mobility for the patient, the level of mobility of the patient including a length of time to exit the bed, wherein the length of time is determined from when the patient is in a position on the patient support structure to when the patient is in a standing position, and wherein the length of time is compared to a range of values;

evaluating a falls risk level of the patient based on the level of the mobility of the patient;

recording the falls risk level of the patient; and automatically implementing a safety measure on the bed based on the falls risk level by arming guard rails on the bed when the falls risk level exceeds a threshold.

9. The method of claim 8, wherein the mobility model is generated by:

observing movements of a plurality of patients for a length of time, each patient being on a patient support system;

determining mobility scores for each of the plurality of patients based on the observed movements;

recording load data from each patient support system for the length of time;

correlating observed movements and mobility scores with patterns of load data; and training a machine-learning algorithm with the load data and corresponding mobility scores to identify patterns of load sensor data indicative of the patient movements corresponding to mobility scores.

10. The method of claim 8, further comprising analyzing the level of mobility in combination with additional patient data to determine the falls risk level for the patient.

11. The method of claim 10, wherein the additional patient data is automatically retrieved from the patient's EMR.

12. The method of claim 10, wherein the additional patient data is received at a computing device from inputs provided by a caregiver.

13. The method of claim 8, further comprising computing a mobility score based on the level of mobility of the patient, and recording the mobility score to an EMR of the patient.

14. The method of claim 13, wherein the mobility score is based on the Get Up and Go Test.

15. The method of claim 10, wherein the falls risk level is determined using the Hendrich II Fall Risk Model.

16. The method of claim 10, further comprising issuing an alert when the falls risk level is high.

17. One or more non-transitory computer-readable media having computer-executable instructions embodied thereon that, when executed by one or more computing devices, cause the one or more computing devices to:

generate a mobility model, including to:

record, over a period of time with a video camera, video images of each of a plurality of patients on respective patient support systems, wherein each of the respective patient support systems is a bed including at least one load sensor having at least two load beams embedded therein and positioned to measure patient movements while lying on the bed;

record, over the period of time with the at least two load beams embedded in the patient support systems, load data for each of the plurality of patients;

analyze the load data and video images with a patient movement analyzer to determine patterns of the patient movements of each patient;

assign a mobility score to each pattern of movement based on a caregiver evaluating the video images corresponding to the pattern of movement with a mobility test; and train a supervised machine-learning algorithm with the load sensor data and corresponding mobility scores to output the mobility model;

evaluate a level of mobility for an individual patient by recording load sensor data from the at least two load beams embedded in a patient support system, the patient support system including the bed on which the individual patient is resting; and analyze the load sensor data with the mobility model, including to:

evaluate the individual patient's fall risk by analyzing the individual patient's mobility level with other factors of a fall risk assessment, wherein the individual patient's mobility includes a length of time to exit the bed before a successful exit of the bed, wherein the length of time is determined from when the patient is in a position on the patient support structure to when the patient is in a standing position, and wherein the length of time is compared to a range of values, and wherein the other factors are determined by one or more of receiving input from the caregiver, accessing information from the individual patient's EMR, and receiving data from a patient monitoring device;

record the individual patient's mobility score and fall risk in the individual patient's EMR; and if the individual patient's mobility score or fall risk exceed a predetermined threshold, automatically implement a safety measure by arming guard rails on the bed and issue an alert to a hospital information system.

\* \* \* \* \*